(12) United States Patent
Camus et al.

(10) Patent No.: US 8,663,300 B2
(45) Date of Patent: Mar. 4, 2014

(54) METHOD AND ASSOCIATED DEVICE FOR POSITIONING A STENT DEPLOYED TO SUPPORT A VESSEL

(75) Inventors: Estelle Camus, Mountain View, CA (US); Oliver Meissner, München (DE); Andreas Meyer, Bubenreuth (DE); Anton Nekovar, Neunkirchen (DE); Martin Ostermeier, Buckenhof (DE); Thomas Redel, Poxdorf (DE)

(73) Assignee: Siemens Aktiengesellschaft, Munich (DE)

( * ) Notice: Subject to any disclaimer, the term of this patent is extended or adjusted under 35 U.S.C. 154(b) by 1282 days.

(21) Appl. No.: 12/075,442

(22) Filed: Mar. 11, 2008

(65) Prior Publication Data

US 2010/0114289 A1 May 6, 2010

(30) Foreign Application Priority Data

Mar. 21, 2007 (DE) .......................... 10 2007 013 624

(51) Int. Cl.
*A61F 2/06* (2013.01)
(52) U.S. Cl.
USPC ........................................................ 623/1.11
(58) Field of Classification Search
USPC ......... 606/108, 191, 192, 194, 195, 198, 200; 623/1.11, 1.12, 1.23; 600/428
See application file for complete search history.

(56) References Cited

U.S. PATENT DOCUMENTS

| | | |
|---|---|---|
| 6,348,048 B1 | 2/2002 | Andrea et al. |
| 2005/0010276 A1* | 1/2005 | Acosta et al. ................. 623/1.11 |
| 2005/0065592 A1 | 3/2005 | Holzer |
| 2005/0182295 A1* | 8/2005 | Soper et al. .................... 600/117 |
| 2007/0055090 A1* | 3/2007 | Neustadter et al. ............... 600/3 |
| 2007/0135707 A1* | 6/2007 | Redel et al. .................... 600/424 |
| 2008/0147173 A1* | 6/2008 | Mciff et al. .................. 623/1.34 |
| 2008/0208184 A1* | 8/2008 | Davies ........................... 606/34 |

FOREIGN PATENT DOCUMENTS

| | | |
|---|---|---|
| DE | 69513506 T2 | 11/1996 |
| DE | 19819634 A1 | 11/1999 |
| WO | WO 2005027820 A2 | 3/2005 |

OTHER PUBLICATIONS

Sebastiaan A. De Winter, Ronald Hamers, PhD, Muzzafer Degertekin, MD, Kengo Tanabe, MD, Pedro A. Lemos, MD, Patrick W. Serruys, MD, PhD, Jos R.T.C. Roelandt, MD, PhD, Nico Bruining, PhD; "Retrospective Image-Based Gating of Intracoronary Ultrasound Images for Improved Quantitative Analysis: The Intelligate Method"; Catheterization and Cardiovascular Interventions; 2004, pp. 84-94; 61:84; Copyright 2004 Wiley-Liss, Inc.

(Continued)

*Primary Examiner* — Ryan Severson
*Assistant Examiner* — Katherine M Shi (57) ABSTRACT

A method for positioning a stent able to be deployed to support a vessel in a blood vessel, especially in the cardiology, with the stent after its provisional placement in a not yet deployed state in an area intended for the support of the vessel, being at least partly automatically deployed as a function of at least one triggering signal for final positioning in the blood vessel.

18 Claims, 3 Drawing Sheets

(56) References Cited

OTHER PUBLICATIONS

Armin Arbab-Zadeh, Anthony N. Demaria, William F. Penny, Robert J. Russo, Bruce J. Kimura, Valmik Bhargava; "Axial Movement of the Intravascular Ultrasound Probe During the Cardiac Cycle: Implications for Three-Dimensional Reconstruction and Measurements of Coronary Dimensions"; Am Heart J 138(5); 1999, pp. 865-873, © 1999 Mosby-Year Book, Inc.

PFM—Produkte für Die Medizin AG, "EVO® Target—Nitinol Stent Implantation System", 2005, pp. 1-4.

Mediguide—Medical Guidance System; "Cardio Vascular MPS ™", Internet: http://www.mediguide.co.il/; 2006.

* cited by examiner

METHOD AND ASSOCIATED DEVICE FOR POSITIONING A STENT DEPLOYED TO SUPPORT A VESSEL

CROSS REFERENCE TO RELATED APPLICATIONS

This application claims priority of German application No. 10 2007 013 624.4 filed Mar. 21, 2007, which is incorporated by reference herein in its entirety.

FIELD OF THE INVENTION

The invention relates to a method for positioning a stent which can be deployed in a blood vessel to support the vessel as well as an associated device and a support system and pressure support system.

BACKGROUND OF THE INVENTION

Arteriosclerotic diseases of the coronary vessels are the most frequent cause of death in the industrialized nations. A widespread cause of a coronary infarction is narrowing of the coronary vessels, so-called stenoses, or lipid-filled so-called "vulnerable plaques".

To treat such conditions a so-called stent, a vessel support which as a rule consists of a wire mesh, is inserted into the stenotized vessel as part of an interventional cardiological measure.

If such a stent is to be positioned in non-critical areas of the blood vessel system this can basically be done without any major problems.

However this situation is different if a stent is to be placed in the vicinity of an ostium or a bifurcation. In such cases the stent must be placed very exactly, in some cases down to within one millimeter.

The problem with such placement however is that the blood vessel system of the coronaries moves with the movement of the heart. The catheter thus moves to a significant extent through the deformation of the heart vessels which occurs when the heart moves, with the speed of movement depending on the heart phase so that it can occur at a lower or a higher speed.

If the placement of a stent in critical vessel areas, i.e. in the vicinity of bifurcations for example, is not exact, the risk of an earlier thrombosis formation then increases possibly with a subsequent embolization. Furthermore restenosis can occur because of turbulences around an imprecisely placed free stent end.

The displacement of a catheter in the vessel which can arise as a result of the periodic movement of the heart can be within the range of up to 6 mm, so that the danger of an inexactly positioned stent can arise here with the associated risks described above.

SUMMARY OF THE INVENTION

The underlying object of the invention is thus to specify an improved method in this connection of the type mentioned at the start for positioning a stent.

To achieve this object there is provision according to the invention, with a method for positioning in a blood vessel of a stent able to be deployed to support said vessel, especially in cardiology, for deployment the stent, after its temporary placement in an area intended for vessel support in a not-yet deployed state, for final positioning in the blood vessel to be at least partly automatic as a function of at least one, preferably electrical, triggering signal.

In advance of the inventive method the stent will thus be temporarily placed by a doctor or by other medical personnel in the area intended for vessel support. To this end the stent is inserted with the aid of a catheter and/or of another suitable medical instrument such as a guide wire into the treatment area. In such cases the stent is not yet deployed, which means that it is not yet in contact with the vessel walls. This is necessary to make it possible to move it to the desired location via the vessel system.

The inventive method essentially relates to this final positioning after this provisional placement has been successfully undertaken. To achieve the final positioning as exactly as possible, i.e. especially to avoid the deviations and problems with positioning ranging in millimeters caused by the heart movement which are caused for example by a different relative displacement of the guide wire and of a stent catheter, in accordance with the invention the final positioning is undertaken by means of at least a partly automatic deployment of the stent. To this end the stent will be at least partly deployed as a function of an electrical signal. Thus an electrical signal is output for example to a control device for stent deployment, which then initiates the deployment process.

The stent is thus deployed with the inventive method without the active intervention of a doctor or other medical personnel. If necessary the partly automatic deployment can be monitored by a technician or a scientist who has specific knowledge of the electrical, i.e. basically physical, signals for the triggering involved.

The automatic deployment of the stent does not have to be complete in such cases. This means that the stent may only be deployed sufficiently to secure its position in the vessel and that the process is final in this sense. This ensures that possible injuries to the vessel with a complete deployment are avoided. Because of this securing the actual stent positioning is independent of the processes which make it absolutely necessary for medical intervention or monitoring.

The stent can be deployed in different ways in such cases. For example self-deploying stent can be used, which assumes its final form after a sleeve is withdrawn which surrounds the stent during its introduction into the blood vessel system. Furthermore or in addition a stent can be used which is deployed as a function of pumping up or inflating a balloon, i.e. by a balloon catheter system. Such an expansion is also considered to be deployment.

The deployment is inventively triggered automatically in each case, if not entirely concluded, so that the correct position in the vessel is assumed.

This means that with the invention the start of the deployment and thereby the fine positioning of a stent through to the fixing in the vessel is achieved solely through measuring signals, i.e. a trigger in particular is achieved by an electrical signal, or other electrical signals, so that with this exact positioning the foundations can be laid for a therapy following on from the inventive method, for which the stent must be completely deployed.

Inventively the stent can be automatically deployed as a function of an electrical signal derived from at least one electrocardiogram and/or for an electrical signal derived from at least one impedance cardiogram and/or from an electrical signal of a stimulator for an external pacing of the heart cycle and/or as a function of at least one electrical signal suitable as a trigger for the stent deployment.

This means that the experience of the cardiologist active in the intervention, who knows the moment in the heart cycle at which he must manually actuate the stent, is no longer needed, but a reliable physical signal is used to initiate the deployment of the stent or to advance it to the point at which its final position is secured. For example on the basis of the ECG (Electrocardiogram) it is possible to detect that a period is currently underway in which there is minimal heart activity, meaning that especially heart cycle is in the diastole, at which point the stent is expanded in precisely the right location as a function of the corresponding ECG signal in the correct heart phase. This optimum period in the diastole only lasts a very few 100 ms, so that only through the automation can the exact positioning be reliably guaranteed.

As well as an ECG signal, signals of an impedance cardiogram or also of a stimulator for an external pacing of the heart cycle can be used. The latter is preferably of interest if the heart cycle, as is generally the case with patients with heart problems, is rather irregular. In this case the accuracy of the stent placement can be increased by a strict periodical external pacing.

Inventively it is possible for a number of said signals to be used in addition to finally initiate the stent deployment. This can be advisable for safety reasons for example. Naturally further electrical signals which are not mentioned can be included if these are suitable to overcome the problems lying in the way of an exact stent placement. With an impedance cardiogram which is recorded with an arrangement of electrodes different from the ECG, an image of the blood circulation processes in the thorax can be created. This means that if necessary, for example as a function of a basic disease of the patient, suitable electrical signals or better suited electrical signals can likewise be recorded for the stent deployment than with the ECG.

Preferably the stent is at least partly automatically deployed as a function of at least one electrical signal lying in the diastolic area of the heart cycle and/or in another area of the heart cycle with small heart movement. Advantageously a heart phase is selected for the expansion or deployment of the stent in which the images for the planning of the positioning, i.e. typically images recorded with an x-ray device, have been created. Mostly an area of the heart cycle with only a small movement is selected for reasons of simpler planning in which the stent deployment can also be undertaken with a low probability of error. Accordingly an electrical signal which is related to the diastolic phase of the heart cycle is especially suitable for deployment the stent. If necessary, within the framework of delay times which can occur while the stent is being deployed, signals can be selected which directly precede the phase of the heart cycle with the small heart movement. This also lies within the field of the invention.

The stent can be at least partly deployed by means of a pneumatically and/or mechanically-acting system.

Air-controlled systems or mechanical systems can also be used to expand or to deploy the stent. It is also conceivable to combine such systems in to a common system which is based on these two activation mechanisms.

For example the stent can be deployed at least partly by means of a balloon catheter system and/or by self-deployment. A balloon is pumped up for example by which the framework of the stent is deployed or expanded until the latter comes into contact with the vessel wall. As an alternative or in addition a self-deployment system can be used in which the stent is folded up until the deployment process is initiated and then, for example, by retraction of a sleeve guaranteeing the original form, assumes its form by itself.

The stent can be automatically deployed at least to the extent where it is in contact with the wall of a blood vessel and/or its position in the blood vessel is fixed. Thus in accordance of the invention the exact (final) positioning of the stent and one which can no longer be changed is obtained in the vessel so that the position of the stent no longer changes with the heartbeat. Subsequently, as part of the actual therapy, the complete expansion can then be undertaken in the desired manner. A deployment of the kind where merely contact to the wall of the blood vessel is established or a first fixing in the desired final position is produced guarantees the security of the automatic deployment. An injury to vessels or other complications can be avoided so that the positioning process does not require any mandatory monitoring by a doctor as part of the process. Only the concluding exact adaptation to the vessel wall which is undertaken after the final positioning in accordance with the inventive method is expediently monitored or undertaken by a doctor.

Accordingly the at least partly automatic deployment of the stent can be supported, especially concluded by a manually-controlled deployment, especially following a first automatic deployment. This manually-controlled deployment is expediently undertaken by a doctor or another specific person with medical training.

Inventively for a stent at least partly deployable by means of a balloon catheter system a pressure support system and/or an electrically and/or manually-controllable pump for pumping up the balloon and/or for a stent deployable by self-deployment a support system for withdrawing a sleeve surrounding the stent can be controlled by the at least one electrical signal. An ECG triggering is also undertaken for example which causes a balloon to be pumped up by an electrically-controllable pump which receives the ECG signal for this purpose. The hand pump previously used is replaced in this case by an automatic system. By using the ECG signal or another defined electrical signal it can be ensured that the stent is located in the intended position for the final positioning. Preferably a trigger signal is used for this purpose which lies in the diastolic area of the heart cycle or, when delay times are taken into account, brings about an expansion in this area.

The electrical signal can alternately or in addition be included for further components of a pressure support system for a balloon catheter, for example for valves of such a system or a control.

With a self-deploying stent the electrical signal can cause the retraction or partial retraction of a sleeve surrounding the stent or of other securing systems which prevent a premature deployment of the stent. To this end the electrical signal can for example be issued to a controller for the retraction mechanism.

For a stent which can be deployed at least partly by means of a balloon catheter system, a pressure support system can be used for the deployment which features a pressure generator, especially an electrical and/or manually-controllable pump, and/or a pressure reservoir and/or a pressure meter and/or a manually-actuatable pressure valve and/or an electrically-controllable pressure valve and/or a control unit.

A corresponding facility for positioning the stent within the framework of an inventive method thus at least partly features the said components. The pressure support system has a pressure generator, e.g. a manually or electrically-controllable pump, as well as a pressure reservoir which if necessary ensures that the pressure after opening valves of the pressure support system does not fall in an undesired manner. A pressure meter can be provided for pressure checking. With a manually-actuatable pressure valve if necessary a desired stent expansion or deployment can be enabled by the doctor, with the opening of the pressure valve able to be forwarded via corresponding signal generators to a processor unit or to other processing means. The enabling of the stent expansion can be undertaken automatically via an electrically-controllable pressure valve. It is thus possible for an electrically-controllable pump together with an electrically controllable pressure valve or a combination of an electrical valve and a manual pump and vice versa to be selected.

For an at least partly self-deploying stent a support system for retracting a sleeve surrounding the stent can be used, which features a spring and/or a manual locking and/or a manually-adjustable stop for setting an initial retraction of the sleeve and/or a holder for removing the sleeve after an initial retraction and/or a planning and/or control unit.

Once enabled, the spring allows a retraction of the stent sleeve at a very high retraction speed to be achieved. Speeds of around 5-50 cm/s are conceivable for example. Via the manual locking for example a mechanical lock can be unlocked at the press of a button, with this unlocking once again able to be notified to the control unit as an electrical signal. Using this electrical signal as the starting point, the part deployment of the stent can subsequently be performed. In this case the trigger would be an electrical signal which does not originate directly from patient but which is generated by a mechanical system for deployment of the stent.

An electrically-controllable locking can for example release a mechanical holder on a corresponding signal. A relay or another circuit operating in a similar manner is conceivable as an electrically-controllable lock.

The length of the initial retraction of the sleeve can be set with the aid of a manually-adjustable stop of the support system. This allows the amount of the stent expansion to be defined in advance.

By means of the holder of the support system, after the initial retraction, i.e. after the part automatic deployment of the stent, the sleeve or another holding device which holds the stent together in a non-deployed state can be finally removed from the stent so that the latter is fully expanded. The holder for removing the sleeve or another means for holding the stent together can for example be removed within the framework of a manual completion of the expansion by a doctor.

The control unit can consist of a processor unit and corresponding interfaces, which the control unit able to be expediently embodied integrated with a planning unit as a planning and control unit. The module can also be a self-contained module which for example receives the data from a separate planning unit for the overall interventional cardiological process, i.e. not only the inventive stent positioning, and has an input for a real-time ECG signal or another electrical signal.

An integrated planning and/or control unit can likewise be provided for the pressure support system described above.

The stent can be deployed at least partly automatically, taking into account and where necessary correcting delay times, especially times for deployment at the stent and/or cable delay times and/or processing times and/or the time for pumping up a balloon and/or the control of a pump for pumping up a balloon and/or the time for retraction of a sleeve surrounding the stent.

These correction times or delays can for example be taken into account and corrected so that a enabling signal, which in the final analysis triggers the partial or automatic deployment directly, is initiated earlier by a corresponding period. Such earlier issuing of the signal is possible since times needed for deployment of the stent as well as cable delay times and suchlike are known or can be determined in advance. It is thus established that the actual expansion or deployment is to be undertaken in a specific area of the heart cycle i.e. at a specific time of the diastole for example, a suitable time for the enabling can be defined correspondingly earlier so that for example as a function of a (manual) enabling of a basic type (basically enabling of the deployment for the next suitable time) is by a technician who is monitoring of the positioning process, in the following cycle of the heart the stent expansion can be initiated at the enabling time for the expansion which takes the delay times into account.

Likewise with a fully-automatic expansion, the process of deployment can be initiated directly, taking account of the delay times. This means for example that a delay time of a system of an electrically-controllable pump with a stent to be expanded by a balloon, with such a delay time lying for example in the millisecond range, can be taken into account.

The inventive method can feature at least some of the following steps:
Planning the final position of the stent,
Provisional placement of the stent depending on the planning,
Real time detection and/or analysis, especially real-time analysis of an electrocardiogram and/or of an impedance cardiogram and/or of a breath curve of the patient,
Enabling the at least part automatic deployment of the stent by a computing device and/or manually by an operator,
For final positioning at least part deployment of the stent after enabling and as a function of the at least one electrical signal and
Where necessary manual and/or operator-supported continuation of the deployment of the stent in the vessel.

The planning of the stent position can in this case be undertaken with a definition of a suitable phase of the electrocardiogram as optimum expansion time. The planning can be undertaken with the aid of a three-dimensional data set which can be created using various methods. The ECG detection can if necessary be undertaken during the entire intervention, i.e. not only for positioning the stent.

The deployment of the stent is expediently dependent on an enabling which can be undertaken by an operator, for example a technician who is responsible for the positioning process. The enabling can be issued manually, if necessary also a by a doctor who is involved in the actual intervention. Depending on the enabling and triggered by an electrical signal (as a supplementary automatic enabling if necessary) the deployment of the stent is undertaken. For reasons of safety the deployment can be initially restricted so that although the stent assumes its final position in the vessel, for further dilation it can still be expanded manually by a further amount. Thus by the final positioning in accordance with the inventive method only the fixing of the stent in the vessel, that is preventing the stent moving with the heart movement, is achieved. The actual medical process of dilation of the vessel or of the effective support can be executed manually by a doctor.

Within the framework of a planning of the final positioning of the stent, depending on the at least one electrical signal with at least one imaging modality, at least one image can be recorded by means of a computing device and/or manually to determine the position of the stent.

The electrical signal in this case is not only used to deploy the stent but is also used for example to trigger an x-ray system or another imaging system in order to detect the position of the stent and the anatomy of a surrounding area at the desired point in time as an image and thus to make possible a precise first positioning before the dilation or deployment. The process of imaging can in this case be undertaken fully automatically by a computing device or control for the imaging modality. Alternately it is conceivable, depending on the electrical signals, i.e. through a forwarding of this signal to a technician who is controlling the imaging, for an image to be recorded manually. A combination of the manual and fully-automatic method is also conceivable, for example a manually-initiated imaging which is then executed automatically.

Within the framework of planning the final positioning of the stent on the computing device side, automatically and/or manually, if necessary supported by the computing device, at least one point in time and/or at least one time interval in the heart cycle for the at least part deployment of the stent can be defined, especially on the basis of an electrocardiogram and/or an impedance cardiogram.

For example a recorded ECG or an impedance cardiogram or the timing of another electrical signal or of a signal which is derived from an electrical signal for triggering the stent deployment can be displayed to an operator on an image output means. The operator can then select a suitable time or a suitable time interval, especially in the heart cycle, which is suitable for the stent expansion. When an interval is selected, on the computing device side a suitable point in time for the stent deployment can be searched for within this time interval, for which purpose of the computing device can refer back to stored data.

Furthermore, in accordance with the invention, a point in time and/or a time interval can be defined and where necessary stored in a memory unit, at which and/or in which by means of at least one imaging modality at least one recorded image for the planning and/or the visualization of the provisional placing and/or final positioning of the stent is created. The point in time or the time interval for the image recording and the stent expansion are preferably selected to be at least largely identical so that the deployment of the stent occurs in the heart phase at which the images have also been created for the planning. This advantageously corresponds to that heart phase at which the stent positioning is later to be visualized.

As part of planning the final positioning of the stent at least one three-dimensional image data set can be recorded by means at least one imaging modality by a computing device and/or manually. In this case the image data recording can be undertaken by the computing device fully automatically or manually, supported by the computing device. In this case the computer support can be embodied so that for example suitable imaging protocols and suchlike are specified by corresponding software or the imaging is undertaken by an operator after an initial start or enabling signal.

In accordance with the invention a three-dimensional image data set can be created from at least two fluoroscopy images and/or computer tomography images, especially angiography images and/or magnetic resonance images and/or intravascular ultrasound images and/or images recorded by means of optical coherence tomography and/or images of an intravascular magnetic resonance imaging and/or images of our other intravascular imaging methods, especially intravascular imaging methods were the least one that integrated positions sensor and/or with parallel position recording based on by planar fluoroscopy images and subsequent reconstruction.

Thus for example at least two fluoroscopy images or a number of fluoroscopy images can be reconstructed into a three-dimensional representation of a section of a vessel he in which the stent is to be deployed. Furthermore for example three-dimensional images can be created from computer tomography data sets, for example combined with magnetic resonance tomography data. As an alternative or in addition intravascular imaging methods can be used which advantageously feature an integrated position sensor or localization system which allows the position or positions to be determined within the vessel system.

A planning of the final positioning of the stent can be undertaken in a separate planning processor unit, especially a planning processor unit of a computing device. This planning processor unit can be equipped with at least one interface to an imaging modality, especially an angiography modality and/or to an electrocardiogram and/or impedance cardiogram unit and/or to a control processor unit and/or with a memory unit, especially for storing planning data recorded within the framework of the planning.

Thus the planning is undertaken in the computer system or in the computing device at a self-contained location, i.e. in a separate processor unit which however is also linked via numerous interfaces to the further systems, for example an angiography system for imaging or another imaging system or an ECG unit and further components. A separate memory unit of the planning processor unit makes it possible to store the planning data not only for the duration of the actual intervention but also for later verification or for a repetition of the examination or a similarly supported examination in another patient.

The planning processor unit can be integrated into an imaging modality, especially an angiography modality. The corresponding device for final positioning of a stent thus features a computing device with such a planning processor unit or an imaging modality respectively, especially an angiography modality which contains such a planning processor unit which has available to it at least some of said interfaces.

For planning the final positioning of the stent an image data set recorded by at least one imaging modality, especially a three-dimensional image data set, can be displayed on an image output means. The data set, for example a three-dimensional data set consisting of a number of fluoroscopy images, is displayed if possible in an optimum manner i.e. where possible without projection-related geometrical truncations and such like. The image can be displayed on a monitor or on a flat screen or on another suitable image output means, if necessary also a combination of a number of image output means such as a screen wall or suchlike.

The type and/or length of the stent and/or the desired position in the image can be selected automatically by a computing device and/or by an operator, especially using at least one signal of at least one position sensor of the stent. An operator such as a doctor or technical personnel also has the opportunity, on the basis of the image displayed, if necessary to select the type and length of the stent before an intervention and to predetermine the desired position which is then decisive subsequently for the final positioning. When position sensors are used the planned sensor position of the stent catheter can be derived and used for the positioning.

A signal recorded by means of at least one electrocardiogram and/or impedance cardiogram unit can be displayed on an image output means. The point in time or the time interval at which the three-dimensional reconstruction was created can be shown in the display of the ECG or an ICG (impedance cardiogram) signal. Likewise the point in time for a subsequent visualization for positioning can be displayed, if the positioning was undertaken with the aid of a static image.

Furthermore in accordance with the invention the breath movement of the patient can be recorded with a sensor and where necessary displayed on an image output means. The sensor can in this case also be a system comprising a number of individual sensors which are used to create a breathing protocol which is displayed on screen.

In the representations of the ECG, ICG and/or the breath curve, at least one point in time and/or time interval of the recording of image data with an imaging modality and/or at least one point in time and/or time interval for the presentation of the positioning can be displayed and/or at least one a point in time and/or a time interval for the deployment of the stent automatically and/or by an operator can be selected. An operator or a computing device thus selects for example by means of an operator tool at a screen with the aid of suitable software a defined ECG time for a stent expansion. Alternately or in the addition a point in time or a time interval in the breath curve can also be selected which is likewise relevant for the movement processes which influence the exact stent positioning. In the breathing curve the time can be displayed at which the visualization is to be undertaken subsequently for positioning of the stent so that this is executed with the aid of a static image.

Furthermore at least one image can be recorded with at least one imaging modality and/or the at least part deployment of the stent can be created or executed during a defined breathing stop phase. In such a case the patient is for example asked automatically by the computing device or by a technician or a doctor to hold their breath at a particular point in time. To this end a computing device can create an optical or acoustic signal. In the normal case the recording of the image or deployment of the stent in a breath holding phase is to be seen as an alternative to an image recording and stent deployment in a defined phase of the breathing cycle. If necessary however a combination can be undertaken such that images are recorded at specific phases of the breathing cycle and in a breath holding phase.

The stent can be positioned with support by an, especially magnetic positioning and/or localization system, especially using virtual and/or real markings and/or sensors. The use of position sensors, for example an electromagnetic sensor system, makes it possible to check the match between the planned position of the stent catheter and the actual position with the aid of the sensor positions. If the planned position is reached a signal can be generated via which the enabling of the stent expansion is undertaken. This can it necessary be the electrical signal for initiating the part automatic expansion.

With the use of position sensors or of a localization system the positioning of the stent catheter can be undertaken by overlaying planning images and the current fluoroscopy images. The stent catheter is then positioned so that the markers currently coincide with the markers defined in the planning image. A static image in a defined ECG phase can be used for this purpose.

For example techniques can be used which, with regard to positioning, are based on virtual landmarks or coils of which allow the detection of the position or a positioning based on their transmit or receive characteristics.

With virtual landmarks it is possible to mark a specific position in a vessel. The marking however is the only stable position in a particular heart phase in the vessel. With a corresponding synchronization of the images with the heart phase a static image with fixed markings can be obtained. If triggering occurs in this heart phase this results in the stent being precisely placed. By using virtual landmarks and sensors the desired placement of the stent can be more easily achieved without contrast media having to be injected over and over again to allow an exact position in the image to be detected and checked or without including a reference image. If corresponding coil sensors are used a further application of radiation can also be dispensed with.

The use of virtual markings and/or of sensors allows the stent to be partly deployed in the time interval and/or at the point in time of the heart cycle in and/or at which the virtual marking and/or the sensor is lying stably in the blood vessel.

As an alternative or in addition the stent can be positioned using contrast media. The disadvantage of this however is that if necessary contrast media has to keep being injected to allow the exact position to be detected.

As part of the placing and/or positioning of the stent at least one image data recording or an image data set created within the framework of the planning can be displayed on an image output means overlaid with a current image data recording. This makes possible a comparison of the planning images with the current images or image data sets in order if necessary to detect a point in time of a coincidence or extensive match which is suitable for a stent expansion.

Likewise the recording of an ECG curve or of an ICG can be overlaid with a current image or be shown as an overlay of a planning image.

When markings and/or sensors of a localization system are used a placement and/or positioning of the stent can be undertaken such that a match between the position and at least one of planned position exists and/or is detected and/or signaled and/or depending on the matching an enabling of a deployment of the stent is defined.

If for example the position of position sensors of an electromagnetic system corresponds to the planned position, which for example can be detected on the basis of an overlaying of the relevant image data, then for example a corresponding facility for final positioning of the stent on the basis of a suitable image processing software can be detected via the computing device that the planned position is reached and if necessary a screen output generated which indicates this to an operator. Alternately, depending on the detection of the desired position, an automatic enabling of a deployment of the stent can be undertaken directly. In this case signaling that the position has been reached can if necessary be undertaken additionally, for example optically or acoustically.

With a real-time detection of an electrocardiogram and/or impedance cardiogram the current heart cycle can be compared to preceding cycles and/or a standard heart cycle, and depending on the results of the comparison, a possible deployment of the stent can be rejected.

A real-time detection of the ECG or ICG can be undertaken continuously during the overall intervention or the positioning process. Similarly conceivable is however a real-time detection only after completion of the planning phase and the provisional placement of the stent. The ECG signal or an ICG can be analyzed in real time, with the signal in its curve being able to be compared with previous signals after the start or the beginning of a cycle. To this end the signals of the patient or also standard signals of a corresponding library of ECG or ICG signals can be used. If strong deviations exist, i.e. the current signal form for example already deviates in the first part of the heart cycle sharply from the form of previous cycles, the deployment of the stent can be initially rejected and the system can wait for the next cycle, the cycle after next or a further cycle. Likewise a real-time recording of a breath curve can be undertaken.

When a balloon system is used an enabling of an at least part deployment of the stent can be provided as a function of guaranteeing an initial pressure and/or for a self-deployment stent as a function of the connection of a support system and/or the setting of an initial retraction path.

The initial pressure which must be guaranteed can be the final pressure for example. A pressure of around 10 bar is conceivable. Also conceivable as initial pressure, which is ensured before the stent deployment is started, is a lower pressure which is sufficient for the stent to achieve a first effective contact through the inflation of the balloon. This could for example be pressure of the order of magnitude of 2 bar. Any injury to the vessel might possibly be avoided by such a lower pressure which leads to only a part deployment of the stent. The initial pressure can be created with an electrically-controlled pump or a hand pump. Only when the initial pressure is available is the deployment enabled.

Accordingly, with a self-deployment stent system, the enabling can be undertaken as a function of the connection of a support system for example with a spring to withdraw a sleeve surrounding the stent. Furthermore, with such a self-deployment system, the setting of an initial retraction path can be required which leads to a first deployment of the stent such that its positioning in the vessel is finally secured, meaning that the position is fixed, with the final further dilatation being able to be undertaken manually.

An enabling can be issued at or by means of a planning and/or control unit for the at least partly automated deployment and/or by the opening of a valve in a support system. If the enabling occurs in the control unit for an automatic expansion then this has the advantage that the processor of the control unit has available to it the corresponding data to the extent where the automatic expansion can be undertaken. In this case the planning and control unit can start the deployment at a suitable point in time directly after the enabling is available.

If on the other hand a valve is to be opened in order to generate the enabling, this process represents a hardware safeguard against unintentional deployment at the stent. In this case a signal can be generated during the enabling which indicates the enabling, which has for example being undertaken manually by a doctor, in the control unit. Afterwards the automatic enabling, i.e. the actual initiation of the stent expansion, can occur at the suitable point in time or time interval.

An electrically-controllable valve and/or a locking mechanism to be opened electrically can be opened by the electrical signal for the at least part automatic deployment of the stent. This automatically starts the first phase of the stent expansion. Delay times can in this case be taken into consideration as described above.

In addition the invention relates to a device for positioning a stent able to be deployed to support a vessel in a blood vessel, especially in cardiology or by means of a method as described above. According to the invention the device features means which are embodied for at least part automatic deployment of the stent for final positioning in the blood vessel as a function of at least one electrical signal after the provisional placement of the stent in an area provided for supporting the vessel in the not yet deployed state. The stent is thus initially provisionally placed, for which purpose the device can likewise feature suitable means, for example a corresponding catheter device as well as a corresponding positioning system in combination with imaging modalities for the monitoring of the provisional positioning. This provisional positioning or placement is undertaken with the stent not yet deployed.

Thereafter the stent is at least partly automatically deployed using corresponding means of the device. To this end a corresponding planning or control unit can be provided which as an integrated unit is responsible both for the planning phase and thus for the provisional placement and also for the final positioning. This planning and control unit, depending on the input of an electrical signal, for example of an ECG, brings about the start of the expansion of the stent, if necessary the start of a part expansion which is sufficient to conclusively fix the stent in the vessel so that the stent is no longer subjected to any movement variations.

As means for at least part automatic deployment of the stent, the device can feature a pneumatic and/or mechanically-operating system, especially a balloon system and/or a system for a self-deploying stent.

The stent can thus be embodied with a balloon or as a self-deploying stent. With a balloon catheter system inflating the balloon causes the deployment or expansion of the stent, with a self-deploying system as a rule a sleeve surrounding the stent or another restriction is removed so that the stent can then deploy in accordance with a previously defined form. In principle a combination of the two systems is also conceivable.

With a balloon system the device can feature a pressure support system and/or with a system for self-deploying stent, a support system for withdrawing a sleeve surrounding the stent. With the pressure support system for a balloon catheter a first automatic part of the stent expansion can for example be undertaken with a predetermined pressure specified by a doctor or a technician which is lower than the finally required pressure for optimum stent placement but however is sufficient for assuming the final position and for establishing contact between the wall and the stent and so that a slippage or movement within the blood vessel is no longer possible.

As an alternative or in addition, with a self-expanding stent which also assumes a predefined form when an external restriction is removed, for example the sleeve preventing stent expansion can automatically be withdrawn by a few millimeters up to its full length which is made possible by a corresponding support system. Such a support system can contain a spring and which makes very rapid retraction of the sleeve possible as well as further locking devices which can be at least in part electrically activated in order to automatically initiate the expansion. An appropriate control unit can be provided for this purpose.

In addition the device can feature at least one imaging modality for if necessary three-dimensional image data detection for the planning of the positioning of the stent and/or the monitoring of the positioning of the stent and/or a planning and/or control unit for the at least part automatic deployment of the stent. If necessary a number of imaging modalities can also be present, for example modalities which make it possible to record computer tomography images as well as magnetic resonance images. If necessary these or further imaging methods can be combined with intravascular imaging methods such as intravascular ultrasound (IVUS) or optical coherence tomography (OCT).

Expediently the device features an electrocardiogram and/or impedance cardiogram unit for recording an electrocardiogram and/or impedance cardiogram, especially in real time and/or a separate planning processor unit, especially with interfaces to other imaging modalities and/or to an electrocardiogram and/or impedance cardiogram unit and/or to a control processor unit and/or a memory unit, especially for storage of planning data recorded within the framework of planning, and/or at least one computing device and/or at least one image output means and/or a positioning and/or localization system for the stent with virtual and/or real markings and/or with an least one sensor and/or means for delivering contrast media and/or a stimulator for an external pacing of a heart cycle patient.

With an ECG or ICG unit it is possible to record the electrical signals of the heart cycle of the patient and to use them as input signals for the at least part automatic deployment of the stent. Expediently the signals are recorded in real time to allow an optimum stent positioning. With a planning processor unit with corresponding interfaces the planning of the final positioning of the stent can be coordinated.

In a memory unit which if necessary can be integrated into the computing device, which in its turn is assigned to an image output means such as a screen or similar, which it necessary can likewise be a component of the computing device, the planning data and further data which is available in respect of the interventional process or the process of positioning the stent can be stored and retrieved as required. The stent can be provided with an electromagnetic or other type of localization system in order to synchronize a planning position with the current position which if necessary is checked by images of the imaging modality, e.g. of an angiography system. If necessary contrast media can be supplied, especially if the method is not operating with virtual markers and suchlike. For patients with a very irregular heart cycle for whom an external pacing is performed, the stimulator for the pacing can be included additionally if necessary in order to obtain the electrical signal for the stent deployment or for the initiation of the stent deployment.

In addition the invention relates to a support system for at least part automatic retraction of a sleeve surrounding a stent for performing a method as described above and to an inventive device with a spring for rapid retraction of the sleeve and/or of a manual locking and/or a manually-adjustable stop for setting an initial retraction of the sleeve and/or a holder for removing the sleeve after an initial retraction and/or a planning and/or control unit.

With the spring it is possible after enabling to with retract the stent sleeve very quickly, for example at the speed of 5 to 50 cm/s. A manual locking allows a mechanical lock to be unlocked at the press the button, with the unlocking able to be notified as an electrical signal to a planning and/or control unit, whereupon the part automatic stent deployment takes place. If necessary an electrically-activatable locking such as a relay can be provided in addition or as an alternative, in accordance with which a mechanical holder is released.

A preferably manually-adjustable stop, an electrically-adjustable stop is also possible however, allows the adjustment of the initial retraction of the sleeve, i.e. the amount by which this sleeve is to be withdrawn in order to bring about the part deployment of the stent. With a holder the doctor or other personal can finally remove this from the stent after the retraction of the sleeve and thus completely expand the latter. The planning and/or control unit can consist of a processor unit and corresponding interfaces. An integration of planning and control is of advantage. A structure with self-contained modules for planning and control respectively is also possible however. In this case the control unit can receive the data from the planning unit. In addition it can feature an input for a real-time ECG or ICG.

Furthermore or as a rule as an alternative, a pressure support system for a balloon system for at least part automatic inflation of the balloon of the balloon system for deployment a stent, especially with a least part deployment, for executing a method as described, or for an inventive device with a pressure generator, especially an electrically and/or manually-operated pump, preferably a dilation pomp and/or a pressure reservoir and/or a pressure meter and/or a manually-actuatable pressure valve and/or an electrically-controllable pressure valve and/or a planning and/or control etc. especially with a programmable delay stage, can be provided or such a device is claimed.

The required pressure is generated with a pressure generator such as a manual or electrical pump. With an electrical pump the electrical signal for the stent deployment can be supplied to the pump directly. A pressure reservoir can be used to ensure that the pressure does not fall disproportionately after valves present in the system have been opened. A pressure meter is used for checking the pressure in the system.

The initial stent expansion can be enabled by a manually-actuatable pressure valve. The valve can pass on the opening which for example is undertaken by a doctor or by technical personnel, to a processor unit, especially a control unit. The stent expansion, after the initial (manual) enabling, is enabled automatically via an electrically controlled pressure valve, so that in this case the stent expansion occurs at the ideal point in time, for example depending on the correct heart phase. The control unit can be embodied as an integrated planning and/or control unit or as a self-contained module. Preferably it features a processor unit with the corresponding interfaces, for example to an imaging modality or with an input for a real-time ECG.

BRIEF DESCRIPTION OF THE DRAWINGS

Further advantages, features and details of the invention emerge with reference to the following exemplary embodiments and also from the drawings. The figures show.

DETAILED DESCRIPTION OF THE INVENTION

Figure 1:
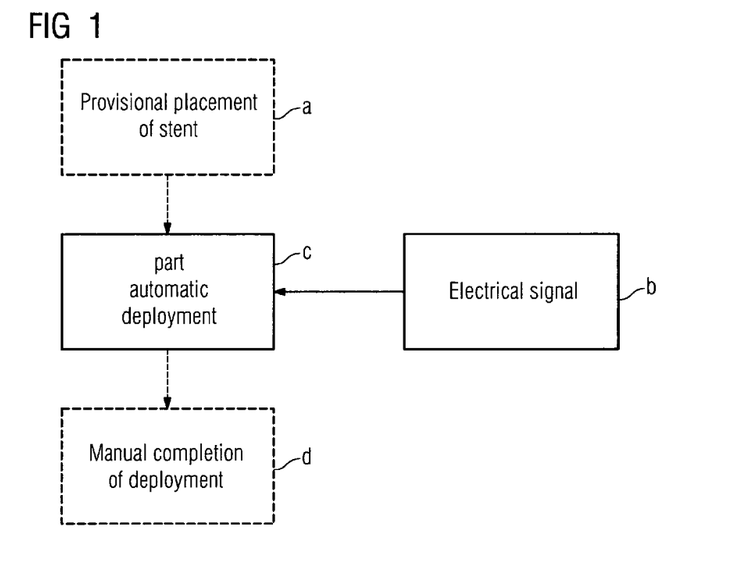
FIG. 1 A basic diagram for incorporation of an inventive method for deployment a stent FIG. 2 an inventive device for positioning a stent in a blood vessel, FIG. 3 a diagram for obtaining an electrical signal for an inventive method from an ECG, FIG. 4 an inventive support system for a self-deploying stent, FIG. 5 an inventive pressure support system for a stent able to deployed with a balloon system, and FIG. 6 a diagram for stent positioning with virtual markers.

FIG. 1 shows a basic diagram for incorporation of an inventive method in deployment of a stent. In this case in accordance with the inventive method depending on an electrical signal issued in step b, in accordance with step c an at least part automatic deployment of the stent by, if necessary also a complete deployment is brought about.

The electrical signal thus acts as an initiator for the stent deployment, i.e. it represents a trigger signal so that the stent at least deploys as far as to assume its fixed final position in the blood vessel. This does not mean that the stent is (mandatorily) completely expanded but merely that it is deployed far enough for it to be supported and thereby fixed on the vessel walls. As a result it is not subject to any influences by movement processes. In particular the stent no longer moves relative to the vessel with the movement of the heart or breathing movement of the patient.

The final positioning is preceded in the normal event, as shown here by the dashed lines in step a, by a provisional placement in an area intended for supporting the vessel. This means that the stent is for example roughly moved in advance or within the framework of the inventive method with a catheter system at least to a point at which it is to be deployed later which is also intended within the framework of an intervention as a support. The dashed lines indicate in this case that this provisional placement is not part of the inventive method in its basic form.

The same applies to manual completion of the deployment in accordance with step d which follows on from the automatic deployment where necessary. The manual completion of the deployment it can be undertaken by a doctor or other personnel. This means that the stent is initially only partly deployed, i.e. for example only far enough for there to be no further danger of vessel injuries being caused by the deployment process. Thus the inventive method can be executed at least in its basic form simply fully automatically or under the supervision of a technician or scientist. The possibly critical medical area is only included later in accordance with step d.

The manual deployment is used, after the final positioning of the stent, to finally deploy it as far as is necessary to achieve an effective support or widening of the vessel.

By the part automatic deployment for example depending on an ECG trigger, a more exact placement of the stent can be achieved. The errors which have previously arisen in such cases through the normal manual deployment by a doctor or by other medical personnel can be largely excluded by the automation. This means that the stent can be positioned as exactly as is required in critical areas in the vessel system, e.g. at bifurcations or in the area of an ostium.

Figure 2:
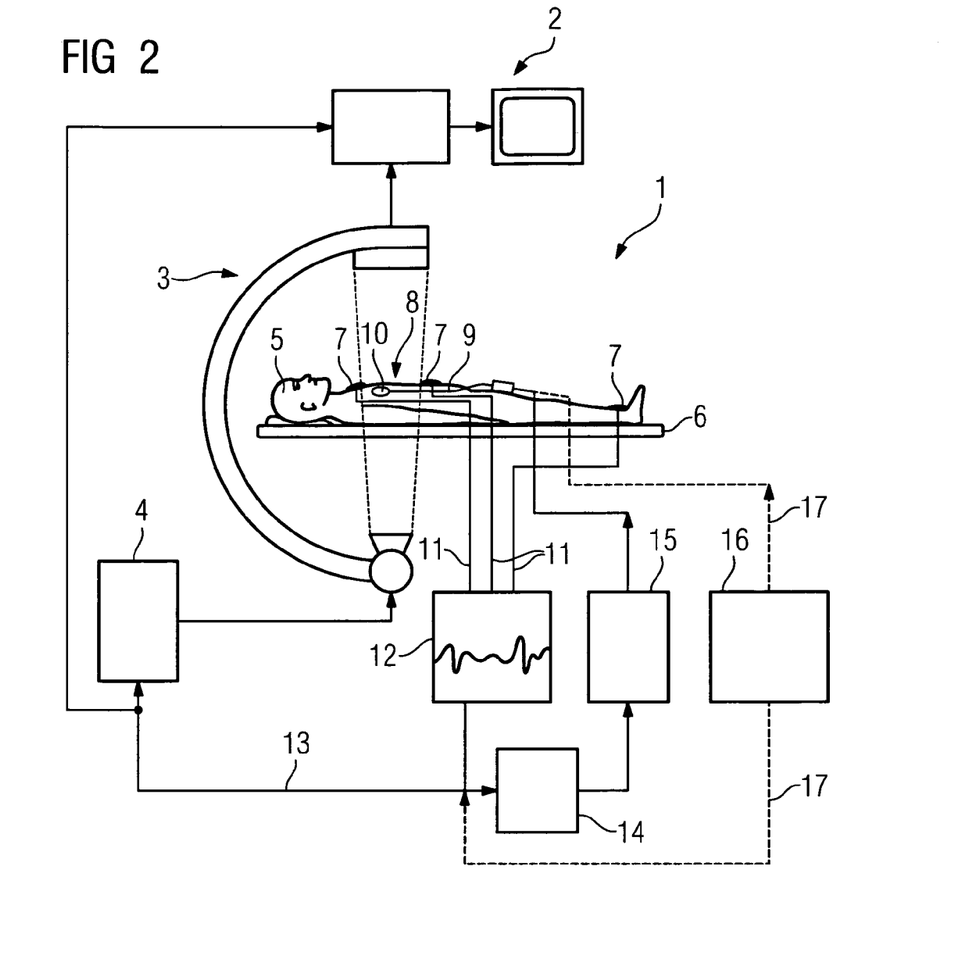

FIG. 2 shows an inventive device 1 for positioning a stent in a blood vessel. The device 1 has an imaging modality 2 with an image output means, which in this case involves an x-ray based modality with a radiation source and detector system 3 on a C-arm. The operation of the imaging modality 2 is made possible with the aid of a generator 4.

With the aid of the imaging modality 2 images of a patient 5 who is located on a patient bed 6 can be created. The images recorded of the patient 5 on the patient bed 6 are first of all prepared within the framework of a planning phase to define a desired placement of the stent or the provisional placement of the stent, which is not shown here, with recorded images being produced later by the imaging modality 2 during the actual positioning in order to check the positioning of the stent.

Various ECG electrodes 7 are provided on the body of the patient of which only a number are shown in this figure. They are used for real-time recording of an electrocardiogram, especially during the positioning of the stent.

The stent in the present case is deployed via a balloon system 8 out of a catheter 9 with the associated balloon 10. To this end the catheter 9 has been introduced into the body of the patient 5. At its tip is located the balloon 10, through the inflation of which the expansion of the stent for supporting the vessel is achieved.

For obtaining the ECG with the aid of ECG electrodes 7 different ECG lines 11 are provided. These lead to an electrocardiogram unit 12. The heart cycle of the patient 5 is monitored in real time with the aid of the ECG unit 12. An electrical signal is selected from the ECG signal of the ECG unit 12 which will be used for expansion of the stent with the aid of the balloon 10. This signal is forwarded as the trigger signal via the supply lead 13 to a delay stage 14 which is programmable and with which delay times can be taken into consideration which are relevant for example for the control of a pump which in the example given here involves a dilation pump 15, or which arise from the inflation of the balloon 10. These times are system-immanent set times or can be determined in advance of the method. This means that the triggering can be undertaken with the aid of the ECG signal of the ECG Unit 12 for a heart cycle in the optimum manner so that the stent expansion is undertaken in an area of small heart movement i.e. in the diastole for example.

For patients 5 with a very irregular heart cycle the signal of a stimulator 16 for an external pacing of the heart cycle can be used as the trigger signal. The signal path in this case is indicated by the dashed-line supply leads 17.

Figure 3:
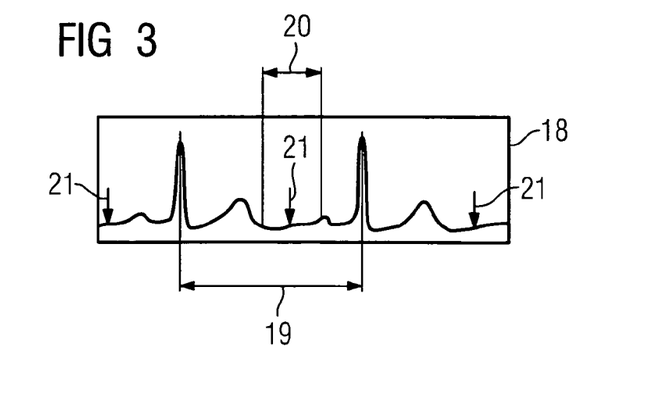

FIG. 3 shows an electrical signal for an inventive method being obtained from an ECG 18. The length of a heart cycle in the ECG 18 is specified in this diagram by the arrow 19.

Different phases occur in a heart cycle in accordance with the arrow 19. For example the diastolic heart phase which involves a heart phase with a comparatively small heart movement, which is indicated in this diagram by the arrow 20 in its length and position. The arrows 21 show the position of the trigger which as electrical signal for the at least part automatic deployment of the stent would be defined in accordance with an inventive method. This can have occurred at a monitor or at another image output means, typically in accordance with FIG. 2, if necessary by a mouse click on the corresponding curve of the ECG 18 displayed on the image output means. If the trigger point is determined in accordance with the arrow 21, in the following heart cycle, after a check if necessary as to whether the heart cycle involved is a regular cycle or if large deviations are occurring, the stent expansion can be undertaken at the predetermined point in time.

Figure 4:
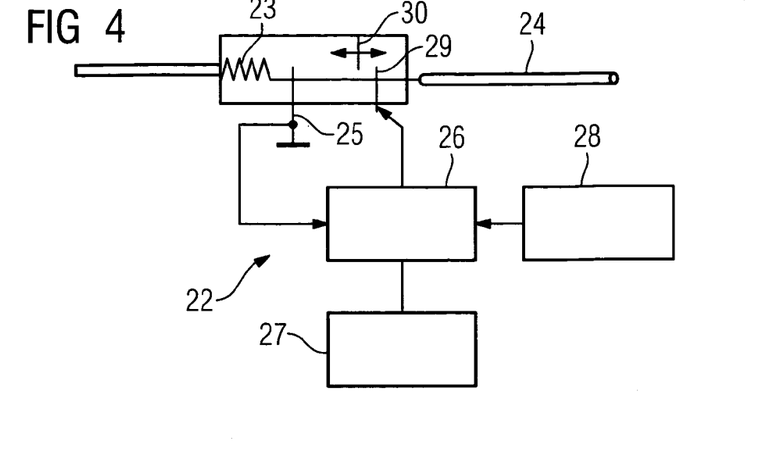

FIG. 4 shows a support system 22 for a self-deploying stent. The stent itself is not shown in the diagram.

The support system 22 features a spring 23 with which after enabling and at a very rapid retraction speed, a retraction of a sleeve 24 surrounding the stent is made possible. In this example the retraction speed of the spring 23 is around a few 10 cm per second.

Furthermore a manual locking 25 is provided with which, at the touch of a button, a mechanical lock is unlocked, with this unlocking being notified as an electrical signal to the planning and control unit 26. Through this manual locking 25 a first enabling on the part of a doctor or of a scientist who is involved with the positioning of the stent can be undertaken such that at the next suitable point in time for an expansion, i.e. the next time that a suitable electrical signal is available, the expansion is actually initiated. For image monitoring or for creating recorded images for the planning, an angiography system 27 is provided which is also controlled by the planning and control unit 26 or which supplies the image data to this unit. The planning and control unit 26 receives an online ECG signal which originates from an ECG unit 28.

Furthermore an electrically-controllable lock 29 is provided, which when a corresponding signal is available, automatically enables the actual stent expansion. This occurs through the release of a mechanical holder, for example through a relay circuit. The corresponding electrical signal is fed to the electrically-controllable lock 29 via the planning and control unit 26.

With the aid of a manually-adjustable stop 30 an initial expansion length for the stent can be set. Not shown here is a holder with which it is possible after the first initial retraction of the sleeve 24, to finally remove this from the stent so that the stent assumes its final deployment stage. The sleeve 24 which prevents an automatic expansion of the stent, is thus partly automatically withdrawn as a function of an electrical signal of the ECG unit 28 so that the stent can finally be positioned in the vessel and for completion or to achieve its vessel-supporting effect, and only then has to be deployed further, with this further deployment not being critical in relation to the positioning since the stent has already been fixed in the vessel by the initial deployment.

Figure 5:
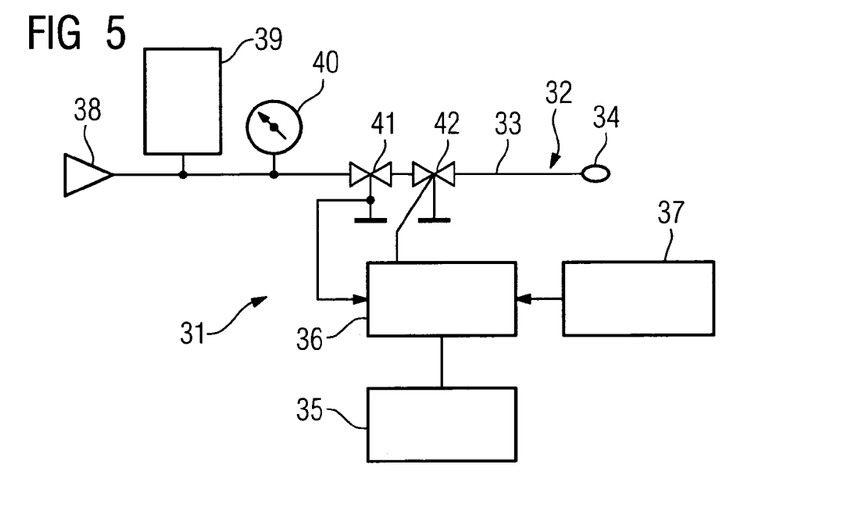

FIG. 5 shows an inventive pressure support system 31 for a stent able to be deployed with a balloon system 32. The balloon system 32 consists of a balloon catheter 33 as well as a balloon 34, through the inflation of which the deployment of the stent is brought about.

An angiography system 35, from which a connection exists to the planning and control unit 36, is provided as imaging modality in the pressure support system 31. The planning and control unit 36 furthermore receives data of an ECG unit which is labeled 37. The ECG unit 37 is embodied for recording an ECG in real time.

A manual pump 38 is provided as the pressures source for inflating that the balloon at 34, with this pumped serving, within the framework of an initial deployment of the stent, to inflate the balloon 34 far enough for contact with the walls of the blood vessel to be established so that a slippage of the balloon in the vessel is no longer possible. In addition a pressure reservoir 39 is provided to safeguard the pressure in the pressure support system 31. The pressure obtaining in the pressure support system 31 is indicated at a pressure meter 40.

In addition of the pressure support system 31 features a manual pressure valve 41 for releasing the stent expansion. Only the basic enabling is provided by the manual pressure valve 41, i.e. the confirmation that, if the electrical signal defined for the purpose is present at the next suitable point in time determined, the stent expansion can be initiated. The opening of the manual pressure valve 41 is passed on to the planning and control unit 36. Depending on the presence of the enabling in accordance with the opening of the manual pressure valve 41, an electrically-activated pressure valve 42 is activated if the corresponding signal of the ECG unit 37 is present so that the part automatic deployment of the stent expansion is enabled. The balloon 34 is then inflated far enough for the stent to assume its final position by fixing it in the vessel.

By manually continuing the process of inflation a further deployment can finally be undertaken so that the support function of the stent is guaranteed.

Figure 6:
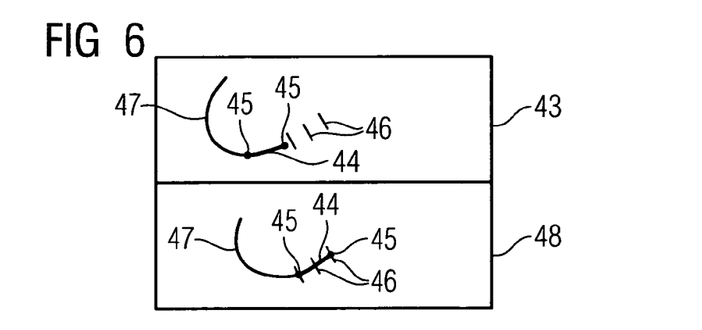

FIG. 6 outlines the positioning of the stent with virtual markers. In this case the first illustration 43 shows the situation in which the stent 44 with the start and end markings 45 which make this detectable in an x-ray image is not yet arranged at the virtual markings 46 which were predetermined within the framework of planning for the final positioning of the stent 44.

The catheter 47 for introduction of the stent 44 into the blood vessel can also be seen. In the illustration 48 the stent 44 is positioned such that the start and end marker 45 with the virtual markings 46 lie above one another or the virtual markings 46 are distributed over the length of the stent 44.

This matching is produced before the expansion of the stent by the heart movement for only one heart phase, namely for the phase in which the planning was undertaken.

If a pump for inflating a balloon for the expansion of the stent is now triggered with the heart phase relevant for the planning, a precisely placed stent 44 is produced which lies on the virtual markers 46 as is shown in illustration 48.

The invention claimed is:

1. A method for positioning a stent deployed for supporting a vessel in a blood vessel of a patient, comprising:
   provisionally positioning the stent in an area in the blood vessel intended for supporting the vessel;
   correcting delay time, wherein the delay time comprises time for deploying the stent, cable delay time, processing time, time for inflating a balloon, time for activating a pump for inflating the balloon, or time for withdrawing a sleeve surrounding the stent;
   partly automatically deploying the stent to a final position in the blood vessel as a function of a triggering signal of the patient considering the delay time;
   defining a point in time or a time interval in the heart cycle;
   storing the point in time or the time interval in a memory unit of a computing device, and
   recording an image of the stent by an imaging modality for detecting a position of the stent at the point in time or the time interval.

2. The method as claimed in claim 1, wherein the partly automatic deployment of the stent is supported by a manually-controlled deployment.

3. The method as claimed in claim 1, wherein the stent is automatically deployed for contacting a wall of the blood vessel.

4. The method as claimed in claim 1,
   wherein the triggering signal is an electrical signal recorded by a device selected from the group consisting of: an electrocardiogram, an impedance cardiogram, a stimulator for an external pacing of a heart cycle, and
   wherein the electrical signal is in a diastolic area of the heart cycle or in an area of low heart movement of the heart cycle.

5. The method as claimed in claim 1, wherein the stent is deployed by a system selected from the group consisting of: a pneumatic system, a mechanical system, a balloon system, and a self-deployment system.

6. The method as claimed in claim 5,
   wherein the balloon system is inflated by a pressure support system comprising an electrically controlled pump or an manually controlled pump,
   wherein the pressure support system comprises a component selected from the group consisting of: a pressure reservoir, a pressure meter, a manually-actuated pressure valve, an electrically-controlled pressure valve, and a control unit connected to an angiography system and an electrocardiogram unit, and
   wherein the stent is deployed when an initial pressure is reached in the balloon system.

7. The method as claimed in claim 5,
   wherein the self-deployment system comprise a support system controlled by the triggering signal for withdrawing a sleeve surrounding the stent,
   wherein the support system comprises a component selected from the group consisting of: a spring, a manual lock, a manually-adjusted stop for setting an initial retraction of the sleeve, a holder for removing the sleeve after the initial retraction, and a control unit connected to an angiography system and an electrocardiogram unit,
   wherein the stent is deployed when the self-deployment system connects the support system or the initial retraction is reached,
   wherein the stent is deployed by the control unit or by opening a valve in the support system, and
   wherein the valve is electrically-controlled by the triggering signal.

8. The method as claimed in claim 1, further comprising:
   planning the final position of the stent by a planning processor,
   provisional positioning the stent based on the planning,
   real-time analyzing the triggering signal,
   enabling the deployment by a computer or an operator, and
   continually deploying the stent in the blood vessel if necessary.

9. The method as claimed in claim 8, wherein the planning processor comprises an interface with the imaging modality or is integrated into the imaging modality.

10. The method as claimed in claim 8, wherein the final position of the stent in the image is selected based on a signal of a position sensor of the stent.

11. The method as claimed in claim 8, wherein the image recoded during the planning is overlaid with a real-time image.

12. The method as claimed in claim 1, wherein a breathing movement of the patient is recorded and displayed on an image output device.

13. The method as claimed in claim 1, wherein the point in time or the time interval for deploying the stent is selected automatically or by an operator.

14. The method as claimed in claim 1, wherein the stent is deployed during a breath-holding phase.

15. The method as claimed in claim 1, wherein the stent is positioned based on a contrast media or a localization system using a virtual or a real marking.

16. The method as claimed in claim 15, wherein the stent is deployed when the virtual marking is stably lying in the blood vessel.

17. The method as claimed in claim 1, wherein the stent is deployed when a position of the stent matches a planned position or when a current heart cycle matches a previous or a standard heart cycle.

18. The method as claimed in claim 1, wherein a type of the stent or length of the stent is selected based on a signal of a position sensor of the stent and the image.

* * * * *